United States Patent

Zhou

[11] Patent Number: 5,597,480
[45] Date of Patent: Jan. 28, 1997

[54] GRADIENT GENERATOR

[76] Inventor: Deming Zhou, 310 Brookwood Dr., Richardson, Tex. 75080

[21] Appl. No.: 229,198

[22] Filed: Apr. 18, 1994

[51] Int. Cl.$^6$ .................................................. B01D 15/08
[52] U.S. Cl. .................. 210/198.2; 210/101; 210/656; 137/262; 137/266
[58] Field of Search .................................. 210/101, 198.2, 210/656, 659; 137/262, 266; 422/70

[56]  References Cited

U.S. PATENT DOCUMENTS

| | | | |
|---|---|---|---|
| 3,398,689 | 8/1968 | Allington | 210/198.2 |
| 3,596,882 | 8/1971 | Hoefer | 137/625.18 |
| 3,815,618 | 6/1974 | Joyce | 137/266 |
| 3,840,040 | 10/1974 | Joyce | 137/266 |
| 3,934,456 | 1/1976 | Munk | 210/198.2 |
| 4,066,879 | 1/1978 | Leaver | 73/61.1 C |
| 4,074,687 | 2/1978 | Joyce | 137/266 |
| 4,202,370 | 5/1980 | Joyce | 137/266 |
| 4,753,892 | 6/1988 | Coombs | 436/18.3 |
| 5,316,540 | 5/1994 | McMannis | 494/37 |

OTHER PUBLICATIONS

Lorentz, K. (1976) Anal. Biochem. 76, pp. 214–220.
Bock, R. M. and Ling, N. S. (1954) Anal. Chem. 26, 1543–1546.
Parr, C. W. (1954) Biochem. J. 56, XXVII–XXVIII.
Anderson, N. L. and Anderson, N. G. (1978) Anal. Biochem. 85, pp. 341–354.
Catalog (1994) p. 69 of Hoefer Scientific Instrument, USA.

Primary Examiner—Ernest G. Therkorn

[57] ABSTRACT

A gradient generator comprising plural vessels of identical height but varied in cross section filled with compositional different liquids, having inlets for filling and outlets connected to a common discharge tube for discharge and delivering; but said plural vessels are formed by plural pieces of non-rigid bags with different profiles arranged side by side and sandwiched within a clearance of an erect parallel plate pair, and has an extrusion means at bottom to extrude and press flat of said filled plural non-rigid bag vessels parallel from their bottom toward the top when said outlets connected to said common discharge tube is at top.

3 Claims, 2 Drawing Sheets

GRADIENT GENERATOR

BACKGROUND OF THE INVENTION a) Field of the Invention

The present invention relates to a gradient generator that delivers compositional varied effluents. Gradient generators are widely used in liquid chromatography, ultracentrifugation, and gel electrophoresis. These are the three most basic methods of separation in biochemical research. More specifically, the present invention relates to an improved gradient generator based on Bock-Ling's disclosure published in 1954 (1).

b) Prior Art and Related Art

The most widely used gradient generator at present is Parr's mixing-chamber gradient generator disclosed in 1954 (2) also. The advantage of Parr's device is that it is simple in structure and can work in both fully filled or partially filled situations; i.e., its capacity is variable, although it is made of rigid material. However, Parr's device can only form simple gradients; the speed of the gradient that can form and deliver is relatively slow, and it also needs motor-driven stirring. Bock-Ling's device, however, delivers effluents whose composition can vary in any controlled and predictable manner. This kind gradient generator has never been widely employed up to now, because the capacity of any given Bock-Ling's device is predetermined, has no flexibility (because it can only start to work when all its vessels are fully filled, and it is made of rigid material), but, on the other hand, the requirements of routine experiments to the capacity of even a given gradient generator are varied from time to time. Moreover, Bock-Ling's device is relatively difficult to manufacture and relatively difficult to clean up after using. In 1977, Andersons (3) first embodied and improved the simplest embodiment of Bock-Ling's disclosure, made its capacity seem more or less adjustable by changing the slope of the baffle in the rectangular tank. This kind gradient generator has only one type and one size, as shown in some company catalogs (4) since the 1980s. Both Parr's and Bock-Ling's devices could hardly work well when the employed gradient-forming liquids have a big difference of density.

U.S. Pat. No. 3,398,689 to Allington disclosed a 2-pump gradient generating apparatus, but it can only form liner gradient. This kind apparatus has been developed into a microprocessor controlled form and is very costly, even though they still can only form simple gradients such as liner gradient, stepwise gradient, or segmented gradient, and cannot form any more complex patterns of composition. In 1976, Lorentz (5) disclosed a method to roughly convert a stepwise gradient into a liner gradient in situ in glass tubes. Ten years later, Coombs employed a microprocessor-controlled motor to do the same job, and obtained U.S. Pat. No. 4,753,892. No device is known, however, that can form gradients accurately when the needed volume is very small.

SUMMARY OF THE INVENTION

The principal object of the present invention is to provide a gradient generator that can form and deliver any controlled and predictable gradient, and has a capacity that is easier to adjust in larger scale.

It also is an object of the present invention to provide a gradient generator that can form and deliver any controlled and predictable gradient more fast and accurately, even the employed gradient forming liquids have a major difference of density, and/or even the total volume of gradient effluent needing to be formed is very small.

A further object of the present invention is to provide a gradient generator that is simple in structure, inexpensive to manufacture and purchase, needs no motor driven stirring, and no need to wash after using.

These and other objects are achieved by the gradient generator presented here that comprises n vessels of identical height but varied in cross-section filled with compositionally different liquids, having inlets for filling, and outlets connected to a common discharging tube for discharge and delivering of the gradient effluent formed therein; but the characteristic is that said n vessels are formed by n pieces of non-rigid bags, such as disposable polyethylene membrane bags with different profiles being arranged side by side and sandwiched within a clearance of an erect parallel plate pair, said clearance can be fixed, or be adjustable, thereby making the capacity of said gradient generator continually adjustable in much larger scale; when said outlets and common discharging tube are at the bottom, said gradient generator discharges under gravitational leveling as usual; however, when said outlets and common discharging tube are at the top, the discharge is performed by a power forced extrusion means to extrude and press flat said n non-rigid bag vessels parallel from the bottom to the top. This makes the gradient effluent faster to form and deliver than the gravity caused discharge, and makes no unwished gravity caused intermixing between different vessels even though said n vessels are filled with very different of density of liquids.

DESCRIPTION OF THE PREFERRED EMBODIMENTS

Figure 1:
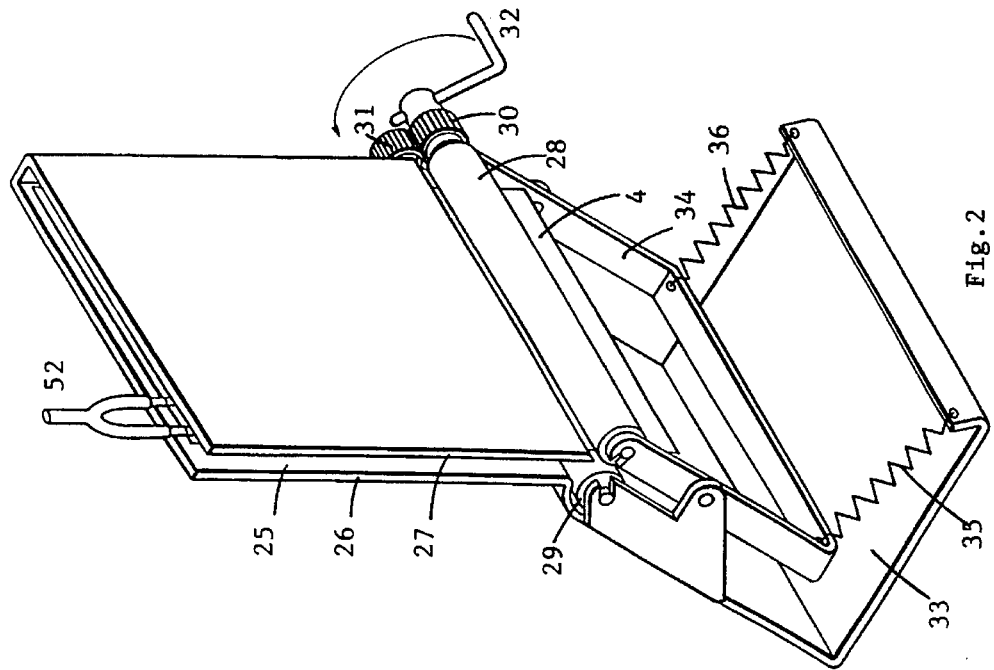
FIG. 1 is a schematic perspective view of a preferable embodiment of the present invention, wherein the plastic membrane bag vessels are sandwiched in an adjustable clearance of an erect parallel plate pair and with their common discharge tube at bottom.

FIG. 1 elucidates the first preferable embodiment of the present invention, wherein 3 is the non-rigid plastic membrane bag vessel complex 3 (see FIG. 3) hanging under the up crossbeam 7 and sandwiched in a clearance 8 of the erect parallel plate pair 9 and 10, wherein 10 is preferably made of light transmissive material such as Plexiglas, 11 is a loop chain looped around the four "sprocket-nuts" 12, 13, 14 and 15; when chain 11 is pulled up or down, it turns said four sprockets-nuts deeper or shallower synchronously, thereby adjusting the thickness of said clearance 8, thus adjusting the capacity of the membrane bag complex 3 sandwiched between of them. In other words, it also means that the capacity of this embodiment of the present invention can be continually adjusted for several folds in this way without need to change any size different membrane bag vessel complex. However, to change the size of different plastic membrane bag complex is also a normal way to adjust the capacity of the present invented gradient generator in its embodiments. In addition, 16, 17, 18, and 19 are four screws fixed on the rare erect plate 9, and has coiled return springs (not shown in FIG. 1 ) placed around said screws 16, 17, 18 19, and clipped in between of said plate pair 9 and 10 as well, 20 is a release valve that controls the two outlets 38 and 39 of two parallel plastic membrane bag vessels (see FIG. 3) simultaneously, 40 is a common discharge tube of said two bag vessels for delivering the gradient effluent formed therein, 21 and 22 are two hooks for supporting said up crossbeam 7; 23 and 24 are two holes for the hanging of the present device.

This embodiment is applicable for gradient elution in liquid column chromatography, which usually is set to run overnight or over a weekend, because this embodiment forms and delivers the gradient effluent rather slowly, but the advantage of the present embodiment is that its discharge dose not have to be power-driven.

Figure 2:
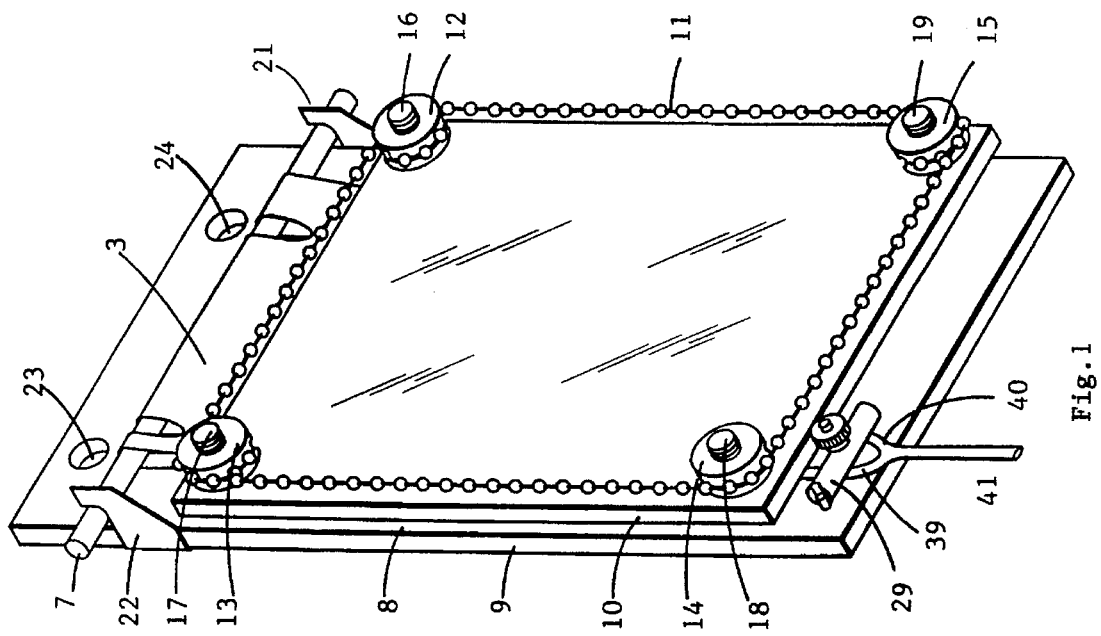
FIG. 2 is a schematic perspective view of another preferable embodiment of the present invention, wherein the plastic membrane bag vessels are sandwiched in a fixed clearance of an erect parallel plate pair and with their common discharge tube at top.
Figure 5:
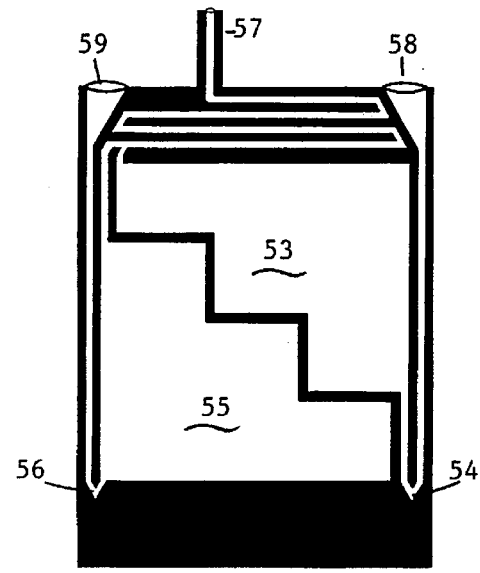
FIG. 5 is a side view of a plastic membrane bag vessel complex consisting of profile different two bags with their outlets at top.
Figure 6:
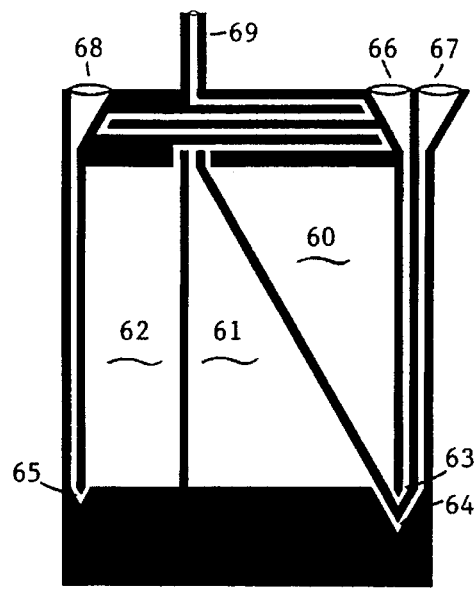
FIG. 6 is a side view of a plastic membrane bag vessel complex consisting of profile different three bags with their outlets at top.

FIG. 2 elucidates the second preferable embodiment of the present invention, wherein 4 is the non-rigid plastic membrane bag vessel complex 4 (referred to in FIG. 4, but can be any other bag vessel complex, such as shown in FIG. 5 or 6) that is sandwiched in clearance 25 of the erect parallel plate pair 26 and 27; said clearance 25 is fixed in the present embodiment, but it can be made adjusted similarly to that elucidated in FIG. 1; Said bag vessel complex 4 with its bottom portion being clipped between a roller pair 28 and 29 at the beginning of operation; said roller pair 28 and 29 are engaged to each other by two gears 30 and 31 axially connected to them; when handle 32 turns, roller pair 28, 29 pull the bag vessel complex 4 down, thereupon to extrude and press flat said two membrane bag vessels from bottom toward the top parallel and gradually, as a result, the contents of the two bag vessels of said complex 4 are extruded through their outlets at the top (see FIG. 4) to the common discharge tube 52 (it cannot be as short as shown in FIG. 2) and are mixed therein to form a compositional varied effluent delivered out therefrom. In addition, 33 is a base rock that supports said plate pair 26, 27 and said roller pair 28, 29 as well; 34 is a U-shaped lever that in cooperation with springs 35, 36 presses said roller pair 28, 29 against each other tightly. Said roller pair 28, 29 is a kind of extrusion means of the present invention, said gear pair 30, 31, handle 32, lever 34 and springs 35, 36 are engaged in this extrusion means. Said roller pair 28, 29 can be motor driven, said motor can be made to be microprocessor controlled as required. This embodiment can form and deliver the gradient effluent much faster than the first embodiment, so that it is ideal for casting pore size gradient gels for electrophoresis and/or to pour density gradient media for ultracentrifugation.

FIG. 3, 4, 5, and 6 show four different samples of plastic bag vessel complex made of two layers of non-rigid plastic membranes, such as polyethylene membrane that is cheapest and is also very good; it makes these plastic membrane bag vessel complexes disposable and reusable. In FIGS. 3–6, the thick sold black lines and black areas indicate where said two layers of plastic membranes are fused to each other.

Figure 3:
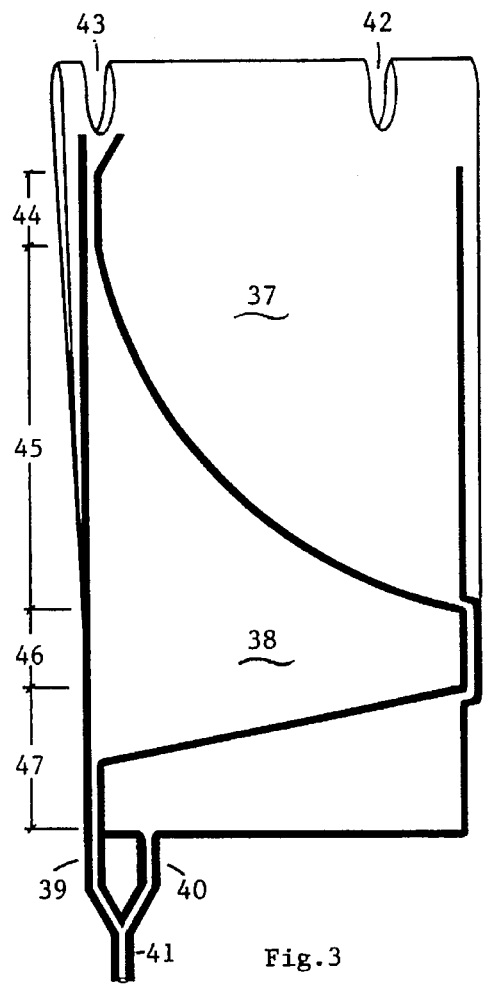
FIG. 3 is a side view of a plastic membrane bag vessel complex consisted of profile different two bags with their outlets at bottom.

FIG. 3 shows a shape of the vessel complex designed for the first embodiment of the present invention as shown in FIG. 1. When it is employed to form gradient for ion exchange chromatography, for example, vessel 37 should be filled with lower salt buffer solution, while vessel 38 should be filled with high salt buffer solution, 39 and 40 are two outlets, 41 is a common discharge tube, 42 and 43 are inlets. During operation, the meniscus in vessel 37 and 38 sweep from top towards the bottom gradually, wherein zone 44 provides a constant low salt buffer solution for the sample loading, then zone 45 provides a concave gradient varied buffer solution from low salt to high salt in order to elute out the components of the sample from the column, zone 46 lets the column to stay in high salt for a period of time thereby making the ion exchange resin to be regenerated, finally zone 47 makes the column to return to lower salt situation and ready for next sample loading.

Figure 4:
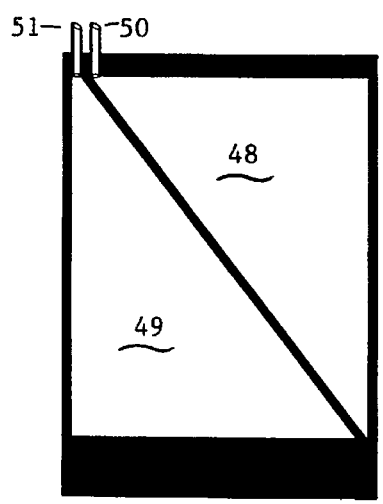
FIG. 4 is a side view of a plastic membrane bag vessel complex consisting of profile different two bags with their inlets are concurrently their outlets at top.

FIG. 4, 5, and 6 show three different shapes of vessel complex desired for the second embodiment of the present invention as shown in FIG. 2.

FIG. 4 shows the vessel complex 4 that forms liner gradient effluents; when in filling operation, the vessel 48, 49 are filled with different liquids from the inlets are concurrent outlets 50, 51 respectively by syringe needle, when in gradient forming operation, a Y-tube 52 (referred to FIG. 2) functionally as the common discharge tube is connected to said inlet-outlet tubes 50, 51. In FIG. 4, said inlet-outlet tubes 50, 51 are made of rigid material, therefore, they need said Y-tube 52 to be made of elastic material, but vice versa. Vessel complex 4 can be made dimensionally as small as a postage stamp without lost its accuracy. Vessel complex 4 can be supplied in pre-filled form upon requirement (but no other gradient generator can).

FIG. 5 shows the vessel complex 5 that forms stepwise gradient effluents, wherein 53 is a vessel, 54 is its inlet 55 is another vessel, 56 is its inlet, 57 is a common discharge tube connected to the outlets of vessels 53, 55 at the top, when discharging said inlets 54, 56 are shut off automatically by the roller pare 28, 29 (referred to in FIG. 2), 58, 59 are two filling funnels.

FIG. 6 shows the vessel complex 6 that is ideal, for example, to form liner gradient effluents for the casting of pore size gradient gel for electrophoresis. In this case, vessel 60 and 61 should be filled with thigh and low concentration of gel forming monomer/dimer solution respectively, while vessel 62 should be filled with pH buffer solution containing the initiator and accelerator of the polymerization process, wherein 63, 64 and 65 are inlets, 66, 67 and 68 are filling funnels of said three vessels respectively; 69 is the common discharge tube connected to the three outlets at the top of said vessels 60, 61 and 62. The reason to make this vessel complex 6 ideal for gradient gel casting, is because in said vessel complex 6, the catalysts (said initiator and accelerator) are isolated from the gel forming monomer/dimer solution; thus, no gel can be polymerized to form within this gradient generator even though the operation process may be delayed by any reason, but it is hardly possible to do so by any other gradient generator.

REFERENCES (1) Bock, R. M. and Ling, N. S. (1954) *Anal. Chem.* 26, 1543.

(2) Parr, C. W. (1954) *Biochem. J.* 56, XXVII.

(3) Anderson, N. L. and Anderson, N. G. (1978) *Anal. .Biochem.* 85, 341

(4) Catalog (1994) p.69 of Hoefer Scientific Instrument, U.S.A.

(5) Lorentz, K. (1976) *Anal.Biochem.* 76, 214.

While preferred embodiments of the present invention have been shown and described herein, such embodiments are obviously provided by way of example only. Numerous variations, changes, and substitutions will occur to those skilled in the art without departing from the invention described herein. Accordingly, it is intended that the invention be limited only by the spirit and scope of the appended claims.

I claim:

1. A gradient generator for delivering an effluent whose composition varies in a controlled and predictable manner in a separation process comprising plural vessels of identical height but varied in cross section filled with compositional different liquids, having inlets for filling and outlets connected to a common discharge tube for discharge and delivering; wherein said plural vessels are formed by plural pieces of non-rigid bags with different profiles arranged side by side and sandwiched within a clearance of an erect parallel plate pair, and has an extrusion means at bottom to extrude and press flat of said filled n non-rigid bag vessels parallel from their bottom toward the top when said outlets are connected to said common discharge tube at the top.

2. The gradient generator of claim 1, wherein said clearance of said erect parallel plate pair is adjustable.

3. The gradient generator of claim 1 wherein said clearance of said erect parallel plate pair is fixed.

* * * * *